US011974501B2

(12) United States Patent
Okamoto et al.

(10) Patent No.: US 11,974,501 B2
(45) Date of Patent: Apr. 30, 2024

(54) CHALCOGEN-CONTAINING ORGANIC COMPOUND, ORGANIC SEMICONDUCTOR MATERIAL, ORGANIC SEMICONDUCTOR FILM, AND ORGANIC FIELD-EFFECT TRANSISTOR

(71) Applicants: THE UNIVERSITY OF TOKYO, Tokyo (JP); PI-CRYSTAL INC., Kashiwa (JP)

(72) Inventors: Toshihiro Okamoto, Tokyo (JP); Junichi Takeya, Tokyo (JP); Masato Mitani, Tokyo (JP); Yosuke Ito, Kashiwa (JP); Tomonori Matsumuro, Kashiwa (JP)

(73) Assignees: THE UNIVERSITY OF TOKYO, Tokyo (JP); PI-CRYSTAL INC., Kashiwa (JP)

( * ) Notice: Subject to any disclaimer, the term of this patent is extended or adjusted under 35 U.S.C. 154(b) by 590 days.

(21) Appl. No.: 17/270,657

(22) PCT Filed: Aug. 29, 2019

(86) PCT No.: PCT/JP2019/034021
§ 371 (c)(1),
(2) Date: Feb. 23, 2021

(87) PCT Pub. No.: WO2020/045597
PCT Pub. Date: Mar. 5, 2020

(65) Prior Publication Data
US 2021/0202865 A1    Jul. 1, 2021

(30) Foreign Application Priority Data
Aug. 31, 2018   (JP) .................................. 2018-163938

(51) Int. Cl.
H10K 85/60    (2023.01)
C07D 333/50    (2006.01)
H10K 10/46    (2023.01)

(52) U.S. Cl.
CPC ....... H10K 85/6576 (2023.02); C07D 333/50 (2013.01); H10K 85/6574 (2023.02); H10K 10/484 (2023.02)

(58) Field of Classification Search
CPC ................ C07D 333/76; C07D 333/50; H10K 85/6576; H10K 85/6574
See application file for complete search history.

(56) References Cited

U.S. PATENT DOCUMENTS

2010/0065826 A1   3/2010  Takimiya et al.
2012/0273768 A1*  11/2012 Ikeda ................. H10K 85/6574
                                                    257/E51.025
(Continued)

FOREIGN PATENT DOCUMENTS

CN    106317071 A    1/2017
JP    2009-9965 A    1/2009
(Continued)

OTHER PUBLICATIONS

Machine language translation of CN 106317071 A (Year: 2017).*
(Continued)

*Primary Examiner* — Erik Kielin
(74) *Attorney, Agent, or Firm* — Birch, Stewart, Kolasch & Birch, LLP

(57) ABSTRACT

Provided is a novel chalcogen-containing organic semiconductor compound having excellent carrier mobility. The compound is represented by Formula (1a) or (1b): [Chem. 1] where in Formulas (1a) and (1b), X represents S, O, or Se, and $R^1$ each independently represents a hydrogen atom, a halogen atom, an alkyl group, an aryl group, an
(Continued)

aralkyl group, a pyridyl group, a furyl group, a thienyl group, or a thiazolyl group.

12 Claims, 11 Drawing Sheets

(56) References Cited

U.S. PATENT DOCUMENTS

| 2013/0245282 A1 | 9/2013 | Takeya et al. |
| 2014/0319494 A1 | 10/2014 | Miyashita et al. |
| 2016/0013425 A1 | 1/2016 | Takeya et al. |

FOREIGN PATENT DOCUMENTS

| JP | 2013-197193 A | | 9/2013 |
| JP | 2014-218434 A | | 11/2014 |
| JP | 2016210752 A | * | 12/2016 |
| WO | WO 2008/050726 A1 | | 5/2008 |
| WO | WO 2014/136827 A1 | | 9/2014 |

OTHER PUBLICATIONS

Machine language translation of JP 2016-210752 A (Year: 2016).*
Kuehm-Caubere, Catherine, et al., "Expeditious and Efficient Syntheses of Pure 4-Methyl and 4,6-Disubstituted Dibenzothiophenes", Tetrahedron, vol. 52, No. 27, pp. 9087-9092 (Year: 1996).*
English translation of International Preliminary Report on Patentability and Written Opinion dated Mar. 11, 2021, in PCT/JP2019/034021.
De et al., "Sulfur Containing Stable Unsubstituted Heptacene Analogs", Orgaic Letters, vol. 14, No. 1, 2012, pp. 78-81.
Fitzgerald et al., "Structure of Diphenanthro[1, 2-b;2', 1'-d]-furan at 191 K", Acta Crystallographica, C49, 1993, pp. 1949-1952.
International Search Report issued in PCT/JP2019/034021 (PCT/ISA/210), dated Nov. 19, 2019.
Murai et al., "Transition-Metal-Catalyzed Facile Access to 3, 11-Dialkylfulminenes for Transistor Applications", Organic Letters, vol. 17, 2015, pp. 708-711.
Written Opinion of the International Searching Authority issued in PCT/JP2019/034021 (PCT/ISA/237), dated Nov. 19, 2019.

* cited by examiner

CHALCOGEN-CONTAINING ORGANIC COMPOUND, ORGANIC SEMICONDUCTOR MATERIAL, ORGANIC SEMICONDUCTOR FILM, AND ORGANIC FIELD-EFFECT TRANSISTOR

TECHNICAL FIELD

The present invention relates to a chalcogen-containing organic compound. The present invention also relates to an organic semiconductor material, an organic semiconductor film, and an organic field-effect transistor.

BACKGROUND ART

The electrical characteristics of organic semiconductors have been inferior to those of inorganic semiconductors such as silicon, but recently, materials having excellent electrical characteristics have been developed, and research pertaining to areas such as the crystal state and carrier mobility has advanced. Compared to the vacuum technique commonly used for inorganic semiconductors, the coating technique for organic semiconductors is advantageous in terms of being low in costs, having a lower environmental burden, and enabling an increased surface area. In addition, production is possible at a temperature near room temperature, which allows a film to be formed on a plastic substrate using printing technology. Thus, the application of organic semiconductors as post-silicon semiconductors in next-generation electronic devices is anticipated.

Increasing the carrier mobility as a characteristic of a semiconductor film is always an important problem regardless of whether the semiconductor film is an inorganic semiconductor film or an organic semiconductor film, and research and development in this area is actively advancing, and in the area of organic semiconductors, polyacene compounds such as pentacene and tetracene are known as organic semiconductors having high mobility. However, polyacene compounds are a group of materials that are difficult to use industrially because they are generally susceptible to light and oxidation. Therefore, in order to improve the chemical stability, numerous compounds in which a chalcogen element such as sulfur or selenium is introduced on a part of an acene skeleton are being examined such as, for example, dibenzothienothiophene and dinaphthothienothiophene.

For the purpose of providing an organic compound that excels in thermal and chemical stability, has semiconductor characteristics (high carrier mobility), and exhibits high solubility in a solvent, Patent Document 1 (WO 2014/136827) proposes a chalcogen-containing organic compound that has an N-shaped molecular structure and is expressed by the following chemical formula.

[Chem. 1]

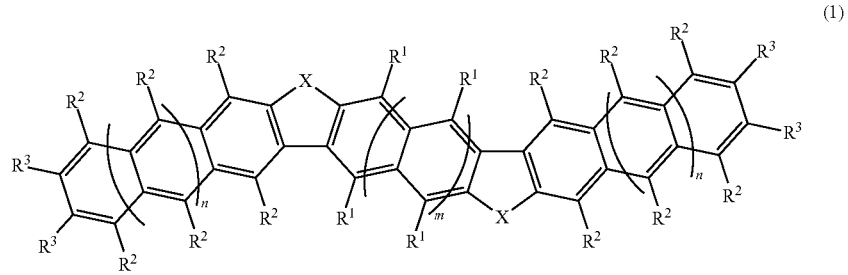

(1)

where in Formula (1), X is each independently oxygen, sulfur, or selenium; m is 0 or 1; the two n are each independently 0 or 1; and $R^1$ to $R^3$ each independently represents hydrogen, fluorine, an alkyl group having from 1 to 20 carbons, an aryl group, a pyridyl group, a furyl group, a thienyl group, or a thiazolyl group; at least one hydrogen in the alkyl group may be substituted with fluorine, and at least one hydrogen on a ring of the aryl, pyridyl, furyl, thienyl, and thiazolyl groups may be substituted with at least one kind selected from fluorine and an alkyl group having from 1 to 10 carbons;

provided that:
(i) in the case of m=0, all of the $R^1$ to $R^3$ may not be hydrogen at the same time;
(ii) when m is 0 and both n are 0, and also when m is 0 and one n is 0 and the other n is 1, a case in which "both X are sulfur and all $R^3$ are the same atoms or groups at the same time" is excluded;
(iii) in the case that m is 0 and both n are 1, all $R^3$ may not be the same atoms or groups at the same time, and at least one $R^3$ is hydrogen.

Patent Document 2 (JP 2013-197193 A) discloses an organic semiconductor compound that is easy to synthesize, is chemically and physically stable, and exhibits high carrier mobility:

[Chem. 2]

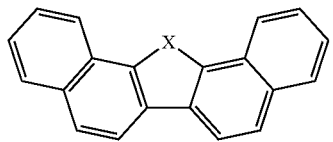

(1)

where in Formula (1), X is oxygen, sulfur, or selenium.

CITATION LIST

Patent Document

Patent Document 1: WO 2014/136827
Patent Document 2: JP 2013-197193 A

SUMMARY OF INVENTION

Technical Problem

As described above, although research of organic semiconductors is steadily progressing, research and development of organic semiconductors is in the midst of expansion. For example, although practical applications of chalcogen-containing organic compounds as organic semiconductor compounds is anticipated, there is still room for research and development, and it is believed that it would be beneficial to develop organic semiconductor compounds that exhibit excellent carrier mobility and have not been reported thus far.

On the basis of such circumstances, an object of the present invention is to provide a novel chalcogen-containing organic semiconductor compound having excellent carrier mobility. Another object of the present invention is to provide an intermediate that is useful for synthesizing such an organic semiconductor compound. Yet another object of the present invention is to provide an organic semiconductor material containing such an organic semiconductor compound. Additionally, another object of the present invention is to provide an organic semiconductor film containing such an organic semiconductor material. Moreover, another object of the present invention is to provide an organic field-effect transistor having such an organic semiconductor film.

Solution to Problem

As a result of diligent research to solve the above problems, the inventors of the present invention discovered that a seven-ring type chalcogen-containing organic semiconductor compound having a prescribed zigzag type structure exhibits excellent carrier mobility. The present invention was completed on the basis of this knowledge, and is exemplified below.

[1]
A compound represented by Formula (1a) or Formula (1b) below:

[Chem. 3]

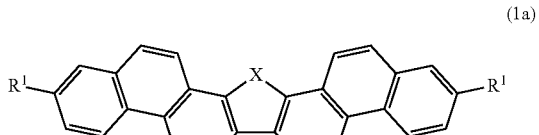

(1a)

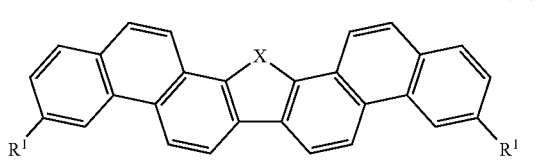

(1b)

where in Formulas (1a) and (1b), X represents S, O, or Se, and $R^1$ each independently represents a hydrogen atom, a halogen atom, an alkyl group, an aryl group, an aralkyl group, a pyridyl group, a furyl group, a thienyl group, or a thiazolyl group.

[2]
The compound according to [1], wherein $R^1$ each independently represents a phenylalkyl group or an alkylphenyl group.

[3]
The compound according to [1], wherein $R^1$ each independently represents a phenylalkyl group having from 7 to 16 carbons, or an alkylphenyl group having from 7 to 16 carbons.

[4]
The compound according to [1], wherein $R^1$ each independently represents a phenylalkyl group having from 7 to 16 carbons.

[5]
The compound according to [1], wherein $R^1$ each independently represents an alkyl group having from 1 to 14 carbons.

[6]
The compound according to [1], wherein $R^1$ each independently represents a halogen atom.

[7]
The compound according to any one of [1] to [6], wherein a temperature at which a weight loss percentage with heating becomes 5% in thermogravimetric measurements when the temperature is increased from normal temperature at a temperature increasing rate of 5° C./minute in a nitrogen atmosphere is 350° C. or higher.

[8]

A compound represented by Formula (X) below:

[Chem. 4]

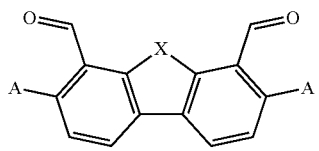

(X)

where in Formula (X), X represents S, O or Se, and A each independently represents a halogen atom.

[9]

A compound represented by Formula (2a) or Formula (2b) below:

[Chem. 5]

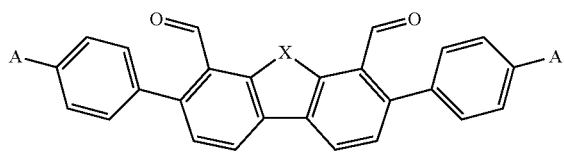

(2a)

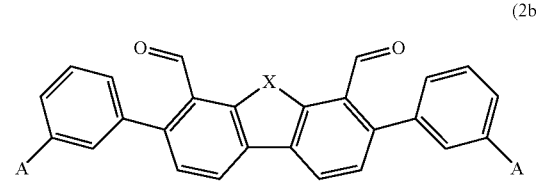

(2b)

where in Formulas (2a) and (2b), X represents S, O or Se, and A each independently represents a halogen atom or a hydrogen atom.

[10]

A compound represented by Formula (3a) or Formula (3b) below:

[Chem. 6]

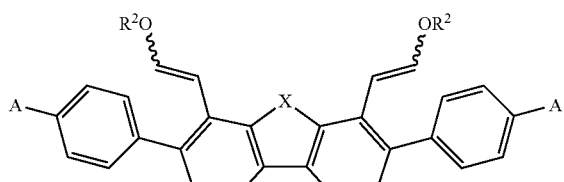

(3a)

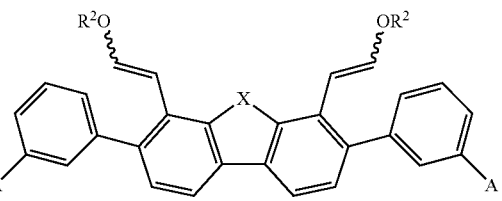

(3b)

where in Formula (3a) or Formula (3b), X represents S, O, or Se, A each independently represents a halogen atom or a hydrogen atom, and $R^2$ each independently represents an alkyl group.

[11]

An organic semiconductor material containing the compound described in any one of [1] to [7].

[12]

An organic semiconductor film containing the compound described in any one of [1] to [7].

[13]

An organic field-effect transistor including a substrate, a gate electrode, a gate insulating film, a source electrode, a drain electrode, and an organic semiconductor layer, wherein the organic semiconductor layer includes an organic semiconductor film described in [12].

Advantageous Effects of Invention

According to one embodiment of the present invention, an organic semiconductor compound exhibiting excellent carrier mobility is provided. In addition, according to a preferred embodiment of the present invention, an organic semiconductor compound exhibiting excellent thermal stability in addition to excellent carrier mobility is provided.

Figure 1:
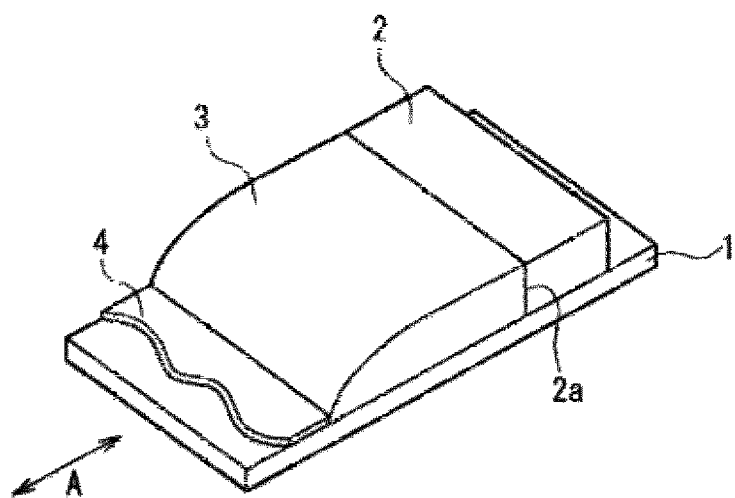
FIG. 1 is a schematic perspective view for explaining the process of an edge-casting method.

DESCRIPTION OF EMBODIMENTS (1. Organic Semiconductor Compound)

According to an embodiment of the present invention, a compound represented by Formula (1a) or (1b) below is provided. The compound thereof exhibits semiconductor characteristics, and therefore can be used as an organic semiconductor material.

[Chem. 7]

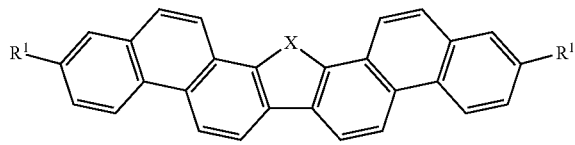

(1a)

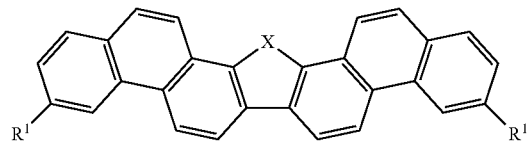

(1b)

where in Formulas (1a) and (1b), X represents S, O, or Se, and $R^1$ each independently represents a hydrogen atom, a halogen atom, an alkyl group, an aryl group, an aralkyl group, a pyridyl group, a furyl group, a thienyl group, or a thiazolyl group.

X is sulfur (S), oxygen (O) or selenium (Se), and from the perspective of obtaining high carrier mobility, X is preferably oxygen (O) or sulfur (S), and is more preferably sulfur (S).

$R^1$ each independently represents a hydrogen atom, a halogen atom, an alkyl group, an aryl group, an aralkyl group, a pyridyl group, a furyl group, a thienyl group, or a thiazolyl group. The two $R^1$ may be the same or different, but from the perspective of ease of synthesis, the two $R^1$ are preferably the same. Examples of the halogen atom include a chlorine atom, an iodine atom, and a bromine atom. Examples of the aryl group include a phenyl group, an alkylphenyl group, a naphthyl group, an alkylnaphthyl group, an anthryl group, an alkylanthryl group, a phenanthryl group, an alkylphenanthryl group, a fluorenyl group, and an alkylfluorenyl group. Examples of the aralkyl group include a phenylalkyl group, a naphthylalkyl group, an anthrylalkyl group, and a phenanthrylalkyl group. Examples of the pyridyl group include a 2-pyridyl group and a 3-pyridyl group. Examples of the furyl group include a 2-furyl group and a 3-furyl group. Examples of the thienyl group include a 2-thienyl and a 3-thienyl group. Examples of the thiazolyl group include 2-thiazolyl.

From the perspective of achieving both high carrier mobility and high thermal stability, preferably, $R^1$ is each independently selected from the group consisting of alkyl groups, phenylalkyl groups, and alkylphenyl groups. Furthermore, when the solubility in an organic solvent is considered, it is more preferable that $R^1$ is each independently a phenylalkyl group or an alkylphenyl group, and even more preferably a phenylalkyl group.

From the perspective of increasing the solubility in an organic solvent and from the perspective of increasing the overlap of π electron orbitals between molecules, when $R^1$ is an alkyl group, an alkyl group having from 1 to 14 carbons is preferable, an alkyl group having from 6 to 14 carbons is more preferable, and an alkyl group having from 7 to 12 carbons is even more preferable. The alkyl group may be a linear or branched chain, and may have a cyclic structure such as a cycloalkyl group, but from the perspective of the molecular arrangement in the crystal, the alkyl group is preferably linear. Specific examples of the alkyl group include a methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, 1-methylpentyl group, 3-methylpentyl group, 4-methylpentyl group, 4-methyl-2-pentyl group, 3,3-dimethylbutyl group, 2-ethyl butyl group, n-heptyl group, 1-methylhexyl group, 3-methyl hexyl group, cyclohexylmethyl group, n-octyl group, tert-octyl group, 1-methylheptyl group, 2-ethylhexyl group, 2-propylpentyl group, n-nonyl group, 3-ethylheptyl group, 2,2-dimethylheptyl group, 2,6-dimethyl-4-heptyl group, 3,5,5-trimethylhexyl group, n-decyl group, 4-ethyloctyl group, 3,7-dimethyloctyl group, n-decyl group, n-undecyl group, 1-methyldecyl group, n-dodecyl group, n-tridecyl group, 1-hexylheptyl group, n-tetradecyl group, n-pentadecyl group, n-hexadecyl group, n-heptadecyl group, n-octadecyl group, n-eicosyl group, cyclopropyl group, cyclopentyl group, cyclohexyl group, 4-methylcyclohexyl group, 4-tert-butylcyclohexyl group, cycloheptyl group, cyclooctyl group, and a cyclononyl group.

From the perspectives of increasing solubility in an organic solvent and increasing the overlap of π electron orbitals between molecules, when $R^1$ is a phenylalkyl group, the phenyl alkyl group is preferably one having from 7 to 22 carbons, is more preferably a phenylalkyl group having from 8 to 18 carbons, and is even more preferably a phenylalkyl group having 8 to 10 carbons. The alkyl moiety in the phenylalkyl group may be linear or branched, or may have a cyclic structure, but from the perspective of molecular arrangement in the crystal, the alkyl moiety is preferably linear. Specific examples of the phenylalkyl group include a benzyl group (phenylmethyl group), a phenethyl group (2-phenylethyl group), a 3-phenylpropyl group, a 4-phenylbutyl group, and a 5-phenylpentyl group.

From the perspectives of increasing solubility in an organic solvent and increasing the overlap of π electron orbitals between molecules, when $R^1$ is an alkylphenyl group, the alkylphenyl group is preferably one having from 7 to 22 carbons, is more preferably an alkylphenyl group having from 8 to 18 carbon atoms, and is even more preferably an alkylphenyl group having from 8 to 10 carbons. The alkyl moiety in the alkylphenyl group may be linear or branched, or may have a cyclic structure, but from the perspective of molecular arrangement in the crystal, the alkyl moiety is preferably linear. Specific examples of the alkylphenyl group include a methylphenyl group (tolyl group), a dimethylphenyl group (xylyl group), a trimethylphenyl group, a tetramethylphenyl group, an ethylphenyl group, and a propylphenyl group.

In one embodiment, the crystals of the compounds represented by Formulas (1a) and (1b) described above can have a herringbone-type packing pattern in which the molecules contact each other at the surface and sides. This packing pattern is advantageous in terms of implementing two-dimensional electrical conduction in an organic thin film.

In one embodiment, the compounds represented by Formulas (1a) and (1b) described above have a temperature at which a weight loss percentage with heating becomes 5% when the temperature is raised in a nitrogen atmosphere from ambient temperature at a temperature increasing rate of 5° C./minute of not less than 350° C. The temperature thereof is preferably 400° C. or higher, more preferably 450° C. or higher, and typically from 350° C. to 500° C.

(2. Method for Synthesizing the Organic Semiconductor Compound)

The organic semiconductor compound described above can be synthesized by, for example, the following schemes.

[Chem. 8]

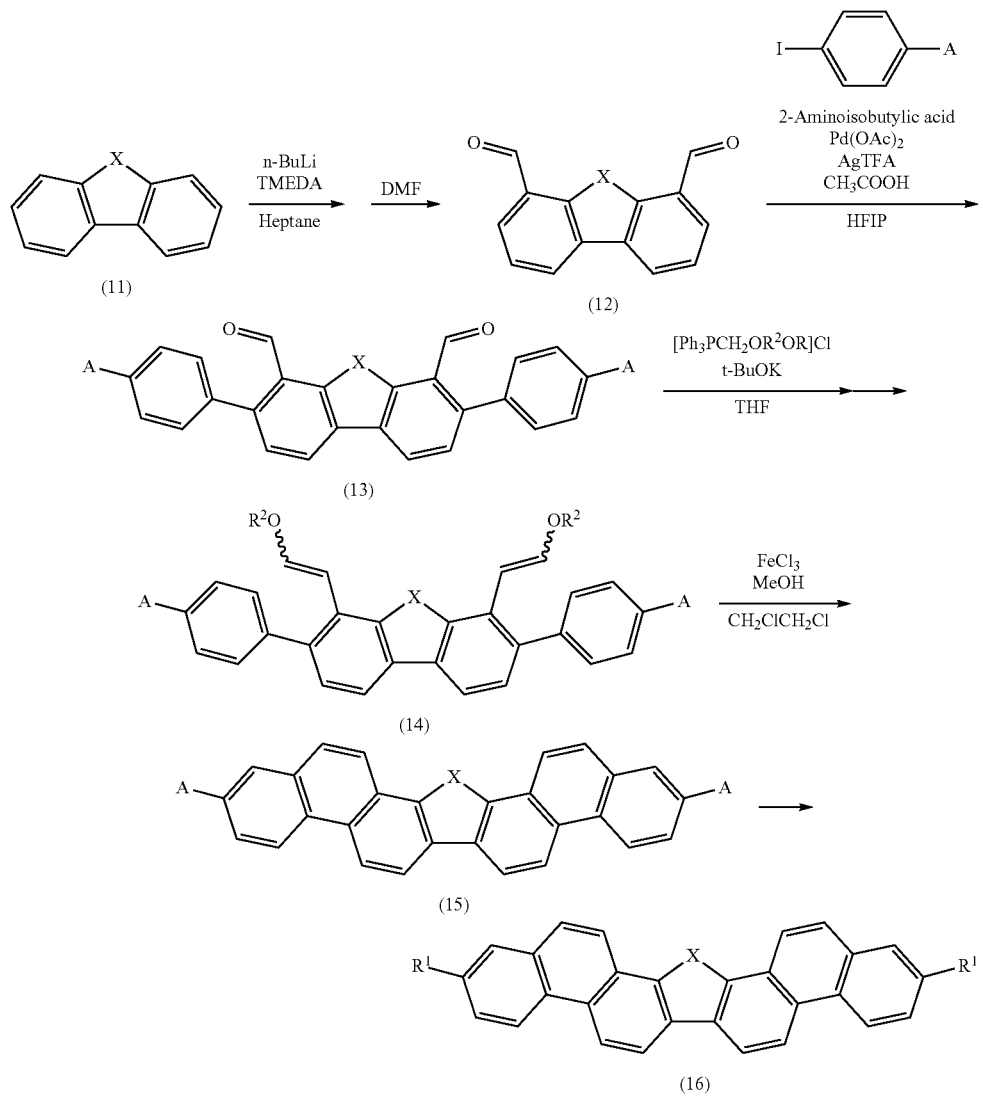

Step 1: Lithiate a tricyclic aromatic compound represented by Formula (11) (example: dibenzothiophene, dibenzofuran) with an organolithium such as n-butyllithium (n-BuLi), and then formylate the product with dimethylformamide (DMF) to obtain a diformyl compound represented by Formula (12).

Step 2: Subject the diformyl compound represented by Formula (12) to an ortho-position-selective C—H activation reaction with a 1-halogen-4-iodobenzene (example: 1-bromo-4-iodobenzene) or iodobenzene using a palladium catalyst to thereby obtain a compound represented by Formula (13) (wherein, A each independently represents a halogen atom or a hydrogen atom). For information regarding the ortho-position-selective C—H activation reaction, refer, for example, to "Diverse ortho-C(sp2)-H-Functionalization of Benzaldehydes Using Transient Directing Groups", J.-Q. Yu et al., J. Am. Chem. Soc. 2017, 139, p. 888.

Step 3: React the compound of Formula (13) with (alkoxymethyl)triphenylphosphonium chloride ([Ph$_3$PCH$_2$OR$^2$]Cl) (where R$^2$ represents an alkyl group) and potassium tert-butoxide (t-BuOK) to obtain a compound of Formula (14) in which the formyl group is vinyl etherified (in Formula (14), A each independently represents a halogen atom or a hydrogen atom). This reaction is generally called a Wittig reaction.

From the perspectives of solubility in the organic solvent used in the synthesis reaction and ease of purification of the target product, the abovementioned R$^2$ is preferably an alkyl group having from 1 to 10 carbon atoms, more preferably an alkyl group having from 1 to 6 carbons, even more preferably an alkyl group having from 1 to 4 carbons, and most preferably a methyl group. The alkyl group may be a linear or branched chain, or may have a cyclic structure such as a cycloalkyl group, but from the perspective of improving the yield in the reaction, the alkyl group is preferably linear. Specific examples of the alkyl group include a methyl group, ethyl group, n-propyl group, isopropyl group, n-butyl group, isobutyl group, sec-butyl group, tert-butyl group, n-pentyl group, isopentyl group, neopentyl group, tert-pentyl group, n-hexyl group, 1-methylpentyl group, 3-methylpentyl group, 4-methylpentyl group, 4-methyl-2-pentyl group, 3,3-dimethylbutyl group, 2-ethyl butyl group, n-heptyl group, 1-methylhexyl group, 3-methyl hexyl group, cyclohexylmethyl group, n-octyl group, tert-octyl group, 1-methylheptyl group, 2-ethylhexyl group, 2-propylpentyl group, n-nonyl group, 3-ethylheptyl group, 2,2-dimethylheptyl group, 2,6-dimethyl-4-heptyl group, 3,5,5-trimethylhexyl group, n-decyl group, 4-ethyloctyl group, 3,7-dimethyloctyl group, n-decyl group, n-undecyl group, 1-methyldecyl group, n-dodecyl group, n-tridecyl group, 1-hexylheptyl group, n-tetradecyl group, n-pentadecyl group, n-hexadecyl group, n-heptadecyl group, n-octadecyl group, n-eicosyl group, cyclopropyl group, cyclopentyl group, cyclohexyl group, 4-methylcyclohexyl group, 4-tert-butylcyclohexyl group, cycloheptyl group, cyclooctyl group, and a cyclononyl group.

Step 4: Cause iron(III) chloride and methanol to act on the compound of Formula (14) to thereby cyclize the vinyl ether moiety and obtain a compound of Formula (15) (where, A each independently represents a halogen atom or a hydrogen atom). For information regarding this cyclization reaction, refer, for example to "Bismuth-Catalyzed Synthesis of Polycyclic Aromatic Hydrocarbons (PAHs) with a Phenanthrene Backbone via Cyclization and Aromatization of 2-(2-Arylphenyl)vinyl Ethers", Murai and Takai et al., Org. lett., 2014, 16, p. 4136.

Step 5: Subject the compound of Formula (15) to a coupling reaction or a dehalogenation reaction to thereby obtain a compound of Formula (16).

As another method, according to the scheme presented below, the hydrogen atoms at the 3- and 7-positions of the diformyl compound of Formula (12) obtained in step 1 are substituted with halogen atoms such as bromine to obtain a compound of Formula (17), after which the halogen atoms are substituted with a phenyl group to obtain a compound of Formula (18), which is then subjected to vinyl etherylation of the formyl group and to cyclization of the vinyl ether moiety, and a compound of Formula (16) is obtained. Other compounds can also be synthesized from the compound of Formula (17).

[Chem. 9]

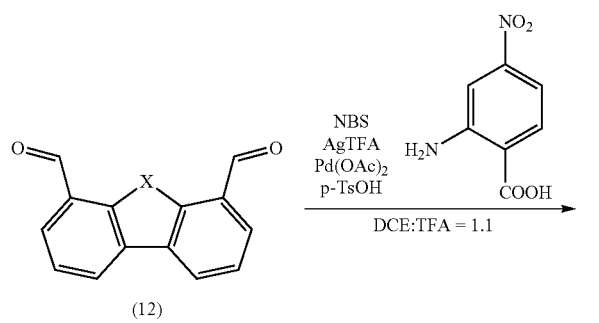

(12)

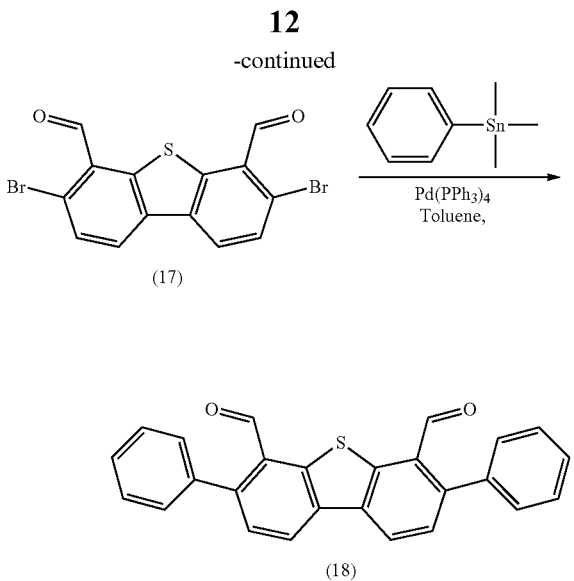

(17)

(18)

In the schemes described above, the bromine atom of the compound represented by Formula (17) may be another halogen atom. Thus, according to an embodiment of the present invention, a compound represented by Formula (X) below is provided.

[Chem. 10]

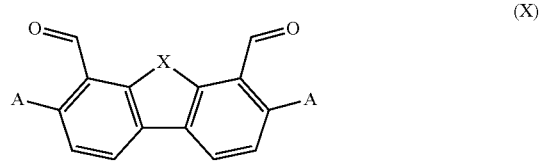

(X)

where in Formula (X), X represents S, O or Se, and A each independently represents a halogen atom.

By using a 2-halogen-4-iodobenzene in place of the 1-halogen-4-iodobenzene in step 2, a compound represented by Formula (13') in which the position of the substituent A is shifted can also be obtained (in Formula 13', A each independently represents a halogen atom or a hydrogen atom).

[Chem. 11]

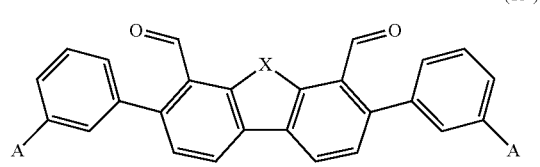

(13')

In this case, a compound of Formula (14') (wherein, A each independently represents a halogen atom or a hydrogen atom) can be obtained in step 3.

[Chem. 12]

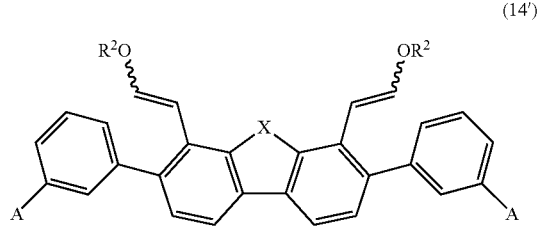

(14')

In addition, a compound of Formula (15') (wherein, A each independently represents a halogen atom or a hydrogen atom) can be obtained in step 4.

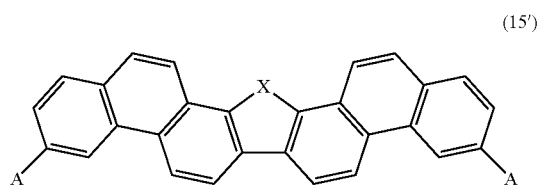

(15')

Finally, a compound of Formula (16') (wherein, A each independently represents a halogen atom or a hydrogen atom) can be obtained in step 5.

[Chem. 14]

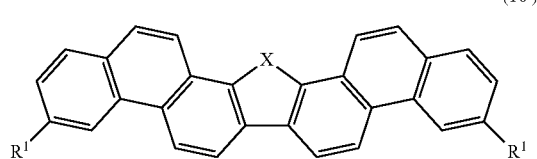

(16')

(3. Formation of an Organic Semiconductor Film)

According to an embodiment of the present invention, an organic semiconductor film containing compounds (organic semiconductors) of Formula (1a) and (1b) is provided. The organic semiconductor film can be formed, for example, by a coating method, a printing method, or a vapor deposition method. Examples of the coating method include a spin coating method, a dip coating method, and blade method. Also, an edge-casting method (refer to Appl. Phys. Exp. 2, 111501 (2009)) and a gap-casting method (refer to Adv. Mater. 23, 1626 (2011)), which were developed by the present inventors and classified as coating methods, are also effective. Examples of printing methods include screen printing, inkjet printing, lithographic printing, intaglio printing, and letterpress printing. Among the printing methods, inkjet printing performed by a printer using a solution of the compound according to an embodiment of the present invention as an ink is a simple method, and thus is preferable.

When the organic semiconductor film is used as is as part of an organic semiconductor element, patterning is preferably implemented by a printing method, and in the printing method, a high concentration solution of an organic semiconductor is preferably used. If a high concentration solution is used, inkjet printing, mask printing, screen printing, offset printing, and the like can be used. Furthermore, when the organic semiconductor film is manufactured by a printing method, the need for a heating and vacuum process is eliminated, and the organic semiconductor film can be produced through a flow operation, which contributes to cost reductions and an increase in responsiveness to process changes. Manufacturing the organic semiconductor film by a printing method also contributes to simplifying the circuit of elements, improving manufacturing efficiency, and reducing the cost and weight of the elements.

Examples of the solvent used in the preparation of an organic semiconductor solution include organic solvents such as 3-chlorothiophene, pentane, hexane, heptane, diethyl ether, t-butyl methyl ether, tetrahydrofuran, methanol, ethanol, isopropanol, ethyl acetate, ethyl lactate, dioxane, benzene, toluene, xylene, dichloromethane, chloroform, 1,2-dichloroethane, dichlorobenzene, acetonitrile, acetone, cyclohexane, cyclopentanone, cyclohexanone, γ-butyrolactone, butyl cellosolve, N-methyl-2-pyrrolidone, N,N-dimethylformamide (DMF), 1,2-dimethoxybenzene, 3-phenoxytoluene, anisole, tetralin, o-dichlorobenzene and dimethylsulfoxide; water; or mixtures of two or more thereof.

The organic semiconductor solution can be produced by introducing an organic semiconductor into a heated solvent or by introducing an organic semiconductor into a solvent and then heating. The form of the organic semiconductor introduced into the solvent is not particularly limited, and can be, for example, in a powder form. From the perspective of stability of the compound, the heating temperature of the solvent is preferably set at the boiling point or lower, and is more preferably set at not more than 10° C. lower than the boiling point, and even more preferably not more than 30° C. lower than the boiling point. Furthermore, from the perspectives of the stability and solubility of the compound, the heating temperature is preferably set at a range from room temperature to 135° C., more preferably from 50 to 135° C., and even more preferably from 70 to 90° C.

Also, from the perspective of obtaining a uniform thin film with good reproducibility, the concentration of the organic semiconductor in the organic semiconductor solution is preferably not greater than 0.2 mass %, is more preferably not greater than 0.1 mass %, and is even more preferably from 0.025 to 0.05 mass %.

The edge-casting method, which is an exemplary film forming method, will be described in detail below. The edge-casting method itself is a known method for forming a film of an organic semiconductor, and is described, for example, in WO 2011/040155 (the entire text of the disclosure of the method thereof is incorporated herein by reference). Preferred embodiments are described below with reference to FIGS. 1 to 4.

As illustrated in FIG. 1, an organic semiconductor solution (hereinafter, also referred to as a "raw material solution") is supplied onto a substrate 1 on which an electrode and insulating film are formed as necessary, and the organic semiconductor solution thus simultaneously contacts an end surface of a contact member 2 and the surface of the substrate 1, and a droplet 3 is formed, In this state, the droplet 3 is dried, and thereby an organic semiconductor film 4 is formed on the substrate 1.

The contact member 2 is placed on the surface of the substrate 1, and has an end surface 2a that stands upright at a predetermined angle from the surface thereof. The end surface 2a is typically planar. The droplet 3 is supplied to contact the end surface 2a of the contact member 2. The contact member 2 can be formed, for example, from a resin, but in addition to a resin, any material may be used as long as the contact member 2 appropriately functions as described below.

Figure 3:
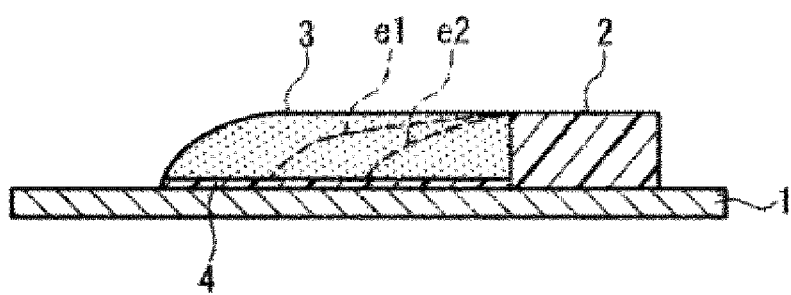
FIG. 3 is a schematic cross-sectional view for explaining the process of the edge-casting method.
Figure 4:
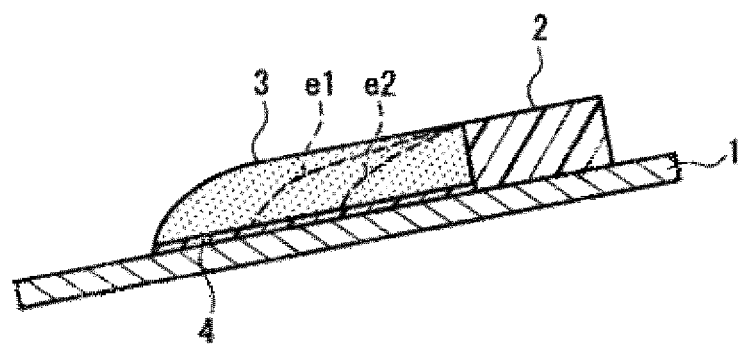
FIG. 4 is a schematic cross-sectional view for explaining a modified example of an edge-casting method.

As illustrated in FIG. 1, in the process of manufacturing the organic semiconductor film, first, the contact member 2 is placed on the substrate 1 with the end surface 2a crossing a predetermined direction A of the substrate 1, and desirably with the end surface 2a being orthogonal to the direction A. Examples of the material of the substrate 1 include, but are not limited to, glass, plastic, ceramic, and metal. In addition, to enhance the wettability of the surface of the substrate 1, the surface thereof is preferably subjected to a treatment through a self-assembled monomolecular film containing a functional group exemplified by an alkyl group, an aryl group, and an amino group. This is because, when a contact angle between the substrate 1 and a distal end portion of the raw material solution with respect to the contact member 2 is small during crystal growth, a more uniform monocrystal film is obtained. This contact angle is preferably not greater than 10°. The substrate 1 may be hard (rigid) or soft (flexible). When a soft substrate is used, a curved organic semiconductor film can be formed. In this state, the raw material solution is supplied onto the surface of the substrate 1, and thus contacts the end surface 2a. The droplet 3 of the supplied raw material solution is held by the end surface 2a, and is in a state in which a constant force is applied. The cross-sectional shape in this state is illustrated in FIG. 3.

Figure 2:
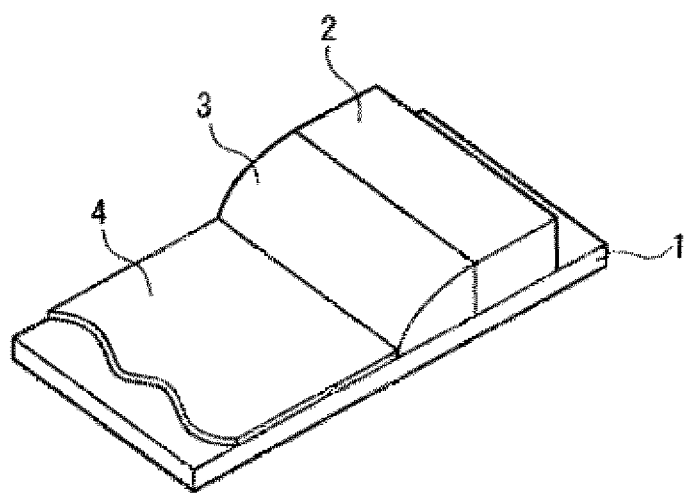
FIG. 2 is a schematic perspective view for explaining a process following that illustrated in FIG. 1.

While the droplet 3 is held by the end surface 2a, a drying process is performed to evaporate the solvent in the droplet 3. As a result, as illustrated in FIG. 3, the solvent in the droplet 3 is evaporated, and thereby the raw material solution becomes sequentially saturated in the direction A at a portion of a distal edge from the end surface 2a, and crystals of the organic semiconductor begin to precipitate. The movement of the distal edge of the droplet 3 in association with solvent evaporation is indicated by the dashed lines e1 and e2. As the organic semiconductor material crystallizes in association with evaporation of the solvent, the organic semiconductor film 4 grows as illustrated in FIG. 2. In other words, crystal growth advances toward the end surface 2a along the direction A of the substrate 1, and the organic semiconductor film 4 is gradually formed.

In this drying process, the direction of crystal growth through contact with the surface 2a is stipulated by the state in which the droplet 3 of the raw material solution is adhered to the end surface 2a. As a result, an effect of controlling crystallinity is obtained, the regularity of the molecular arrangement of the organic semiconductor is improved, and it is thought this contributes to an improvement in electron conductivity (mobility).

While dependent on the type of organic semiconductor, the drying process can be carried out in air at a substrate temperature from 60 to 90° C., and typically from 70 to 80° C. The film formation rate depends on the type of organic semiconductor, but can be set to approximately 15 to 25 μm/s. Furthermore, the film thickness can be adjusted by changing the substrate temperature and the concentration of the organic semiconductor in the solution. In the case of a continuous edge-casting method described below, the film thickness also varies depending on the movement speed of the contact member.

As a modified example of the manufacturing method described above, as illustrated in FIG. 4, the substrate 1 is tilted and maintained at a predetermined angle, and the contact member 2 is placed on the substrate 1 with the end surface 2a crossing the tilting direction of the substrate 1, and desirably with the end surface 2a being orthogonal to the tilting direction. In this state, the raw material solution is supplied onto the surface of the substrate 1, and thus contacts the end surface 2a. The droplet 3 of the supplied raw material solution is held by the end surface 2a, and is suspended in the tilting direction of the substrate 1. By tilting the substrate 1, the size of the surface wetted by the droplet 3 is controlled, and an organic semiconductor film with desired characteristics is easily obtained.

Note that the method of forming the droplet 3 is not limited to the method described above. For example, a droplet attached to the end surface 2a can be formed by immersing the substrate 1 along with the contact member 2 in the raw material solution, and then removing the substrate and contact member therefrom.

Figure 5A:
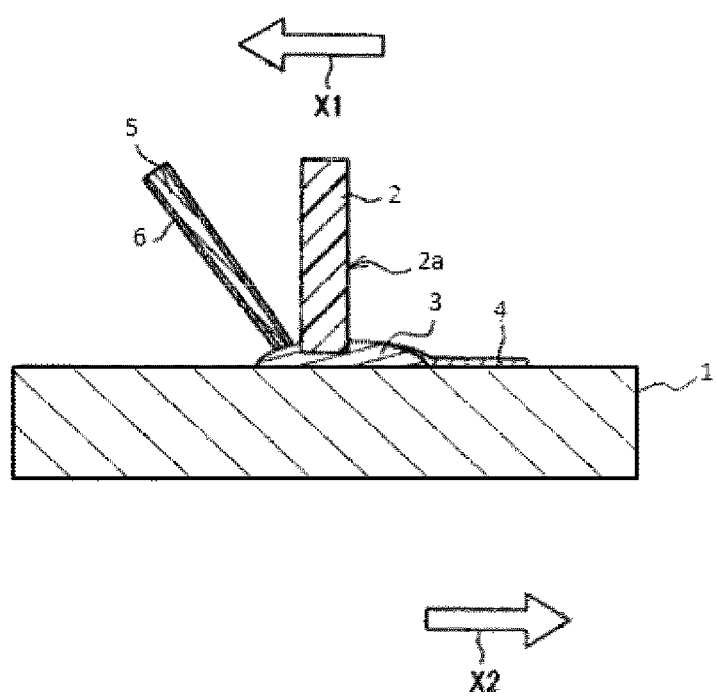
FIG. 5A is a schematic cross-sectional view for explaining the process of a continuous edge-casting method.
Figure 5B:
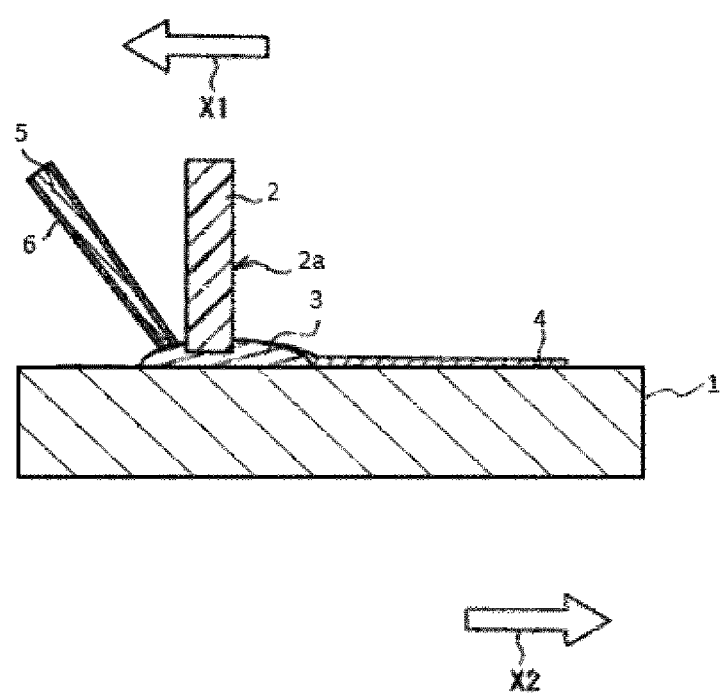
FIG. 5B is another schematic cross-sectional view for explaining the process of the continuous edge-casting method.

Another modified example is a method based on a continuous edge-casting method. The continuous edge-casting method is introduced in "Inch-Size Solution-Processed Single-Crystalline Films of High-Mobility Organic Semiconductors" (Junshi Soeda et al., Applied Physics Express 6, The Japan Society of Applied Physics, 2013, 076503), and is an advantageous method for enlarging the surface area of a monocrystalline film. In the continuous edge-casting method, as illustrated in FIGS. 5A and 5B, the raw material solution 5 is continuously supplied while moving the substrate 1 and the contact member 2 relative to each other in directions (directions indicated by X1 and X2 in FIGS. 5A and 5B) in which the contact member 2 is separated from the droplet 3, the directions thereof being parallel to the surface of the substrate 1. Thereby, the organic semiconductor film 4 is continuously formed on the substrate 1 after the solvent in the droplet 3 has been evaporated and the contact member 2 has been moved. The raw material solution 5 can supplied using, for example, a solution supply nozzle 6. As illustrated in FIGS. 5A and 5B, the contact member 2 is provided with a slight gap between the surface of the substrate 1 and the bottom surface of the contact member 2, and the tip end of the nozzle 6 is arranged at a surface of the contract member at a side opposite the end surface 2a of the contact member, and thereby the raw material solution 5 can be supplied towards the gap.

According to this method, the raw material solution 5 is continuously supplied, and therefore the growth of crystals does not end due to evaporation of the solvent from the raw material solution 5. Accordingly, the organic semiconductor film 4 to be formed can be formed with a desired size on a desired large surface area according to the width of the end surface 2a of the contact member 2 and the movement distance.

During the above relative movement, from the perspective of maintaining a constant film thickness of the organic semiconductor film 4, it is desirable to continue supplying the raw material solution 5 and maintain the size of the droplet 3 within a predetermined range. That is, the droplet 3 is maintained at the same dimension by supplying the raw material solution 5 at a speed equivalent to the evaporation speed of the solvent. Because the speed of crystallization from the raw material solution 5 is approximately from 1 mm/min to several cm/min according to a normal setting, the relative speed of the substrate 1 and the contact member 2 may be adjusted to the same speed. Through these operations, when the state illustrated in FIG. 5A has progressed to the state illustrated in FIG. 5B for example, the organic semiconductor film 4 is continuously formed on the surface of the substrate 1 after the contact member 2 has moved.

(4. Organic Semiconductor Film)
<4-1. Carrier Mobility (Average Value)>

Mobility is an important characteristic that governs the response speed of the semiconductor device. In one embodiment, the organic semiconductor film according to the present invention can have an average mobility of 5 cm$^2$/Vs or greater, and preferably has an average mobility of 7 cm$^2$/Vs or greater, more preferably an average mobility of 8 cm$^2$/Vs or greater, and even more preferably an average mobility of 10 cm$^2$/Vs or greater, and can have an average mobility of, for example, from 8 to 12 cm$^2$/Vs.

In the present invention, the mobility is calculated based on a typically implemented FET mobility evaluation method (FET method). That is, the FET current equation of:

$$Id = (W/2L) \cdot \mu \cdot Cox(Vg-Vt)^2 \ldots \text{for case of a saturated region}$$

(wherein, Id: drain current, Vg: gate voltage, Vt: threshold voltage, µ: mobility, Cox: oxide film capacitance, W: channel width, L: channel length) is converted into an equation relating to the mobility p, and the mobility is determined from the measurement values of the IdVg of the FET.

<4-2. Film Thickness>

The film thickness required for the organic semiconductor film differs depending on the application, and thus is not particularly limited, but ordinarily, it is desirable that the film be thin in order to reduce resistance other than in the channel region. In one embodiment, the average film thickness of the organic semiconductor film according to the present invention can be set to 1 µm or less, in another embodiment, the average film thickness can be set to 100 nm or less, and in yet another embodiment, the average film thickness can be set to 50 nm or less. In one preferred embodiment, the organic semiconductor film according to the present invention can have an average film thickness of 20 nm or less, in another embodiment, the average film thickness can be set to 15 nm or less, and in yet another embodiment, the average film thickness can be set to 10 nm or less.

(5. Organic Semiconductor Element)

In accordance with an embodiment of the present invention, an organic semiconductor element having an electrode and the abovementioned organic semiconductor film is provided. Specifically, the organic semiconductor film and elements having other semiconductor characteristics can be combined to form an organic semiconductor element. Elements having other semiconductor characteristics include, for example, rectifying elements, thyristors performing switching operations, triacs, and diacs.

The organic semiconductor element can also be used as a display element, and in particular, a display element in which all members are constituted by an organic compound is useful.

Examples of the display element include flexible sheet-like display devices (for example: electronic paper, IC card tags), liquid crystal display elements, and electroluminescent (EL) elements. These display elements can be produced by forming, on an insulating substrate formed from a polymer exhibiting flexibility, the organic semiconductor film and one or more layers including constituent elements that cause the film to function. The display element produced by such a method is flexible, and therefore the display element can be carried in a pocket of clothing, a purse, or the like.

Examples of the display element include a unique identification code-responding device. The unique identification code-responding device is a device that reacts to electromagnetic waves having a specific frequency or a specific code, and responds with electromagnetic waves containing a unique identification code. The unique identification code-responding device is used as a means to identify documents or individuals in applications such as a reusable passenger ticket or membership card, a payment settlement means, a seal for identifying luggage or goods, a role of a tag or stamp, and in company or administrative services.

The unique identification code-responding device has, on an insulating substrate formed from a flexible polymer or a glass substrate, an antenna for reception synchronized with signals, and an organic semiconductor element according to an embodiment of the present invention that operates with received power and returns an identification signal.

(6. Organic Field-Effect Transistor (FET))

An example of the organic semiconductor element according to the present invention is an organic field-effect transistor (organic FET). The organic FET can be used in combination with a liquid crystal display element and an electroluminescent (EL) element.

In one embodiment, the organic FET according to the present invention includes a substrate, a gate electrode, a gate insulating film, a source electrode, a drain electrode, and an organic semiconductor layer, and the organic semiconductor layer is constituted by an organic semiconductor film according to an embodiment of the present invention. The organic FET may have a carrier injection layer to increase the efficiency of carrier injection.

In an organic FET, the voltage applied to the gate electrode is controlled, and thereby a carrier is induced at the organic semiconductor layer interface on the gate insulating film, the current flowing to the source electrode and the drain electrode can be controlled, and switching operations can be performed.

Generally, organic FET structures are broadly classified into bottom gate structures and top gate structures, which are further classified into top contact structures and bottom contact structures.

As organic FETs, an aspect in which a gate electrode is formed on a substrate, and the gate insulating film and the organic semiconductor layer are formed thereon in this order is referred to as a bottom gate type; and a structure in which an organic semiconductor layer, a gate insulating film, and a gate electrode are formed in this order on a substrate is referred to as a top gate type.

As the organic FET, an aspect in which the source electrode and the drain electrode are disposed at a lower portion (substrate side) of the organic semiconductor layer is referred to as a bottom contact type FET; and an aspect in which the source electrode and the drain electrode are disposed at an upper portion of the organic semiconductor layer (on the side opposite the substrate with the organic semiconductor layer interposed therebetween) is referred to as a top contact type FET. From the perspective of carrier injection between the source electrode and drain electrode and the organic semiconductor layer, the top contact type structure often has more superior organic FET characteristics than the bottom contact structure.

Various substrates can be used as the substrate. Specific examples include glass substrates, metal substrates such as gold, copper, and silver, crystalline silicon substrates, amorphous silicon substrates, triacetyl cellulose substrates, norbornene substrates, polyester substrates such as polyethylene terephthalate substrates, polyvinyl substrates, polypropylene substrates, and polyethylene substrates.

Examples of the material of the gate electrode include Al, Ta, Mo, Nb, Cu, Ag, Au, Pt, In, Ni, Nd, Cr, silicons such as polysilicon, amorphous silicon, and highly doped silicon, inorganic materials such as tin oxide, indium oxide, and an indium tin compound (indium tin oxide: ITO), and organic materials such as electrically conductive polymers. The electrically conductive polymer may of course be treated to improve conductivity by adding impurities.

Examples of the material of the gate insulating film include inorganic materials such as $SiO_2$, SiN, $Al_2O_3$, and $Ta_2O_5$; and polymeric materials such as polyimides and polycarbonates.

The gate insulating film and the surface of the substrate may be surface treated using a known silane coupling agent such as, for example, a silane coupling agent having an alkyl group, such as hexamethyldisilazane (HMDS), octadecyltrichlorosilane (OTS), decyltriethoxysilane (DTS), and octadecyltriethoxysilane (ODSE), or a silane coupling agent having a fluoroalkyl group, such as triethoxy tridecafluorooctyl silane (F-SAM). When an appropriate surface treatment is performed using HMDS, OTS, DTS, ODSE, F-SAM, or the like, ordinarily, effects such as an increase in the size of the crystal grains constituting the organic FET layer, an improvement in crystallinity, and an improvement in molecular orientation are observed. As a result, a trend occurs in which the carrier mobility and on/off ratio improve, and the threshold voltage decreases.

As the materials of the source electrode and the drain electrode, the same type of material as that of the gate electrode may be used, the same material as that of the gate electrode may be used, a different material than that of the gate electrode may be used, or different types of materials may be laminated.

The carrier injection layer is provided in a form contacting any of the source electrode and drain electrode, and the organic semiconductor layer as necessary to increase the carrier injection efficiency. The carrier injection layer is formed using, for example, tetrafluoro-tetracyanoquinodimethane (F4TCNQ), hexa-aza-triphenylene hexa-carbonitrile (HAT-CN), and molybdenum oxide.

EXAMPLES

Examples (invention examples) according to an embodiment of the present invention are presented below in conjunction with comparative examples. The examples are provided to facilitate a better understand of the present invention and its advantages, and are not intended to be limiting.

Example 1: Diphenanthro[1,2-b:2',1'-d]thiophene

Step 1: Dibenzothiophene (1.0 equivalent), n-butyllithium (2.0 equivalents) and tetramethylethylenediamine (TMEDA) (3.0 equivalents) were added to a heptane solvent and refluxed and lithiated at 0° C. for 15 minutes. Next, dimethylformamide (DMF) was added, the mixture was formylated at room temperature for 1 hour, and 4,6-diformyldibenzothiophene was obtained.

[Chem. 15]

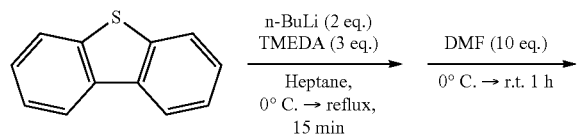

-continued

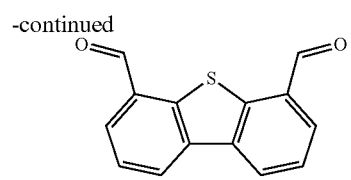

Step 2: The 4,6-diformyldibenzothiophene (1.0 equivalent), 1-bromo-4-iodobenzene (6.0 equivalents), 2-aminoisobutyric acid (0.8 equivalents), palladium (II) acetate (0.2 equivalents), silver trifluoroacetate (AgTFA) (3.7 equivalents), and acetic acid (20.0 equivalents) were added to a hexafluoroisopropanol (HFIP) solvent and reacted for 48 hours at 110° C., and the following (3,7-bis (4-bromophenyl)-4,6-diformyldibenzothiophene) was obtained (yield of 66%).

[Chem. 16]

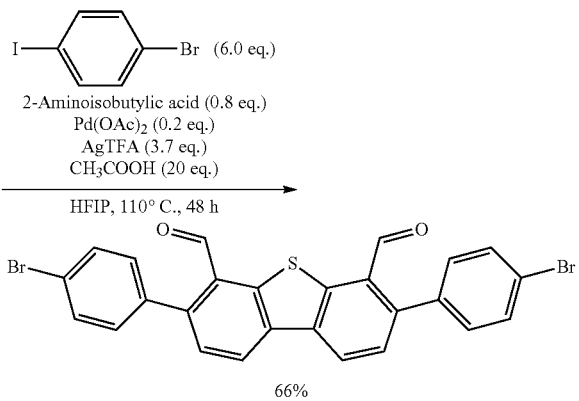

66%

Step 3: The compound (1.0 equivalent) obtained in step 2, (methoxymethyl)triphenylphosphonium chloride ([Ph$_3$PCH$_2$OMe]Cl) (4.0 equivalents), and potassium tert-butoxide (t-BuOK) (4.0 equivalents) were added to a tetrahydrofuran (THF) solvent and reacted for 10 minutes at 0° C., and then further reacted for 16 hours at room temperature, and the following compound (3,7-bis (4-bromophenyl)-4,6-bis (methoxyethenyl)dibenzothiophene) with a vinyl etherified formyl group was obtained (yield of 61%).

[Chem. 17]

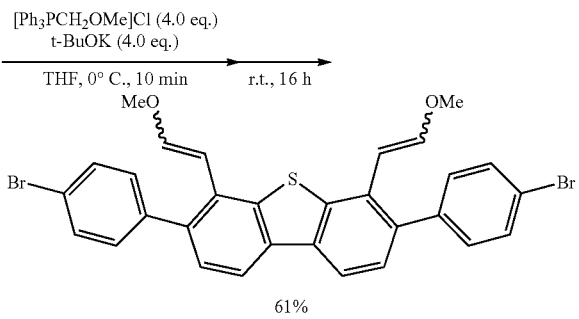

61%

Step 4: The compound (1.0 equivalent) obtained in step 3, iron (III) chloride (0.1 equivalents) and methanol (1.0 equivalent) were added to a 1,2-dichloroethane solvent and reacted at 80° C. for 3 hours, and the following compound (4,13-dibromo-diphenanthro[1,2-b:2',1'-d]thiophene) having a cyclized vinyl ether moiety was obtained (yield of 84%).

[Chem. 18]

FeCl₃ (0.1 eq.)
MeOH (1.0 eq.)
―――――――――――→
CH₂ClCH₂Cl, 80° C., 3 h

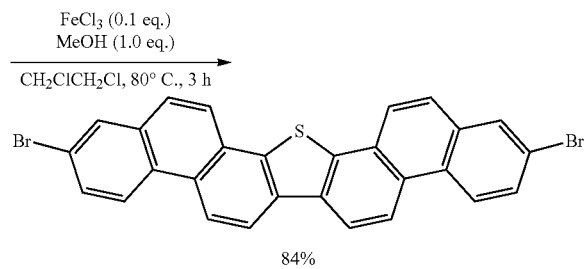

84%

Step 5: The compound obtained in step 4 and palladium carbon (Pd/C) (10 mass % Pd) were added at equal amounts to a tetrahydrofuran solvent and stirred for 30 hours at room temperature in a hydrogen atmosphere, and the following compound (diphenanthro[1,2-b:2',1'-d]thiophene) was obtained (yield of 53%).

[Chem. 19]

debromination
―――――――→

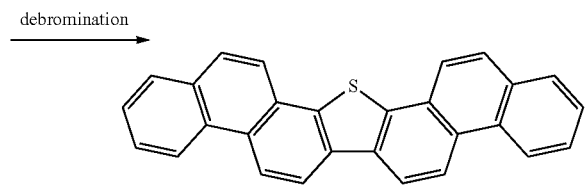

Figure 6:
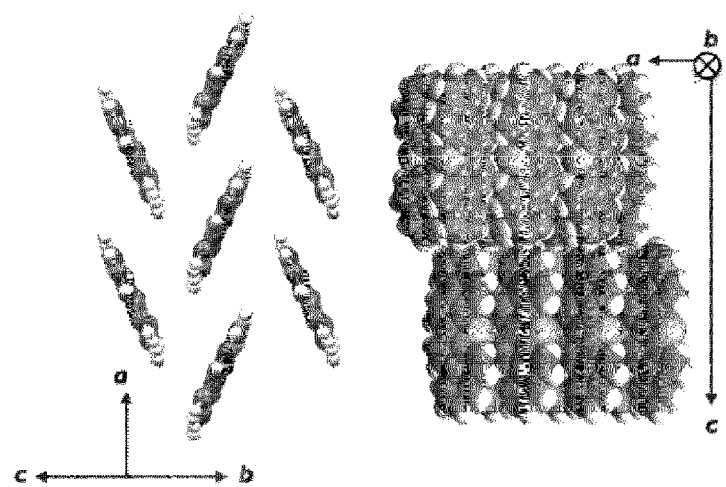
FIG. 6 illustrates the crystal structure and provides crystal data of a compound of Example 1.

A monocrystal of the compound obtained in step 5 was obtained by a physical vapor transport (PVT) method, and a monocrystal X-ray structural analysis was performed using the R-AXIS RAPID II curved imaging plate monocrystal automatic X-ray structure analyzer available from Rigaku Corporation. As a result, it was confirmed that the monocrystal of the compound had a herringbone structure-type packing pattern. FIG. 6 illustrates the crystal structure of the compound and provides crystal data thereof.

The compound obtained in step 5 was subjected to thermogravimetry-differential thermal analysis (TG-DTA). For the measurements, a high vacuum-differential-type thermal balance (Rigaku Thermo Plus EVO II TG 8120, available from Rigaku Corporation) was used. The temperature was increased at a temperature increase rate of 5° C./minute from normal temperature under a nitrogen flow (100 sccm) at atmospheric pressure, and the temperature ($T_{95}$) at which the weight loss percentage with heating was 5% was determined. The results are shown in Table 1.

Figure 10:
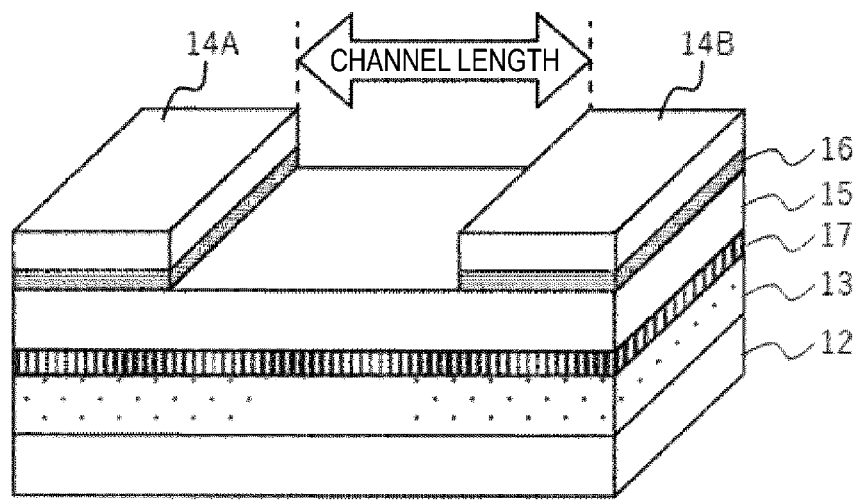
FIG. 10 is a cross-sectional schematic view illustrating an example of a bottom gate-top contact type organic thin-film transistor.

A bottom gate-top contact type organic thin-film transistor having the structure illustrated in FIG. 10 was produced with the compound obtained in step 5, and the characteristics thereof were evaluated. As illustrated in FIG. 10, this organic thin-film transistor included a gate electrode 12, an insulating film 13, a source electrode 14A, a drain electrode 14B, an organic semiconductor film 15, a carrier injection layer 16, and a self-assembled monomolecular film 17. The structure of the organic thin-film transistor was the same in all of the examples and comparative examples.

<Production and Evaluation of Polycrystalline Organic Thin-Film Transistor>

As a substrate for measuring FET characteristics, a substrate having a thermal oxide film of $SiO_2$ was prepared on a surface of a silicon substrate (thickness: 0.4 mm). The surface of the thermal oxide film of this substrate was treated with octyltrichlorosilane.

Next, the compound obtained in step 5 was vacuum deposited at a thickness of 30 nm onto the substrate for measuring FET characteristics, and then 80 nm of gold was vapor deposited as an electrode using a shadow mask. The obtained transistor was annealed at 100° C., after which the transmission characteristics were measured by sweeping the gate voltage in a range from +20 V to −60 V at a drain voltage of −60 V using the 4200-SCS semiconductor parameter analyzer (available from Keithley Instruments, LLC). From the obtained transmission characteristics, the carrier mobility in the saturation region was determined from the IdVg measurement of the FET described above. The evaluation results are shown in Table 2.

Example 2: 4,13-diphenyl-diphenanthro[1,2-b:2',1'-d]thiophene

Steps 1 to 4 were implemented in the same manner as in Example 1, after which phenylmagnesium bromide (3.0 equivalents) was added to the toluene solvent, the mixture was cooled to 0° C., and then zinc chloride (3.2 equivalents) and lithium chloride (3.2 equivalents) were added, and the mixture was stirred at 0° C. for 10 minutes. Next, the compound (1.0 equivalent) obtained in step 4 and a [1,1'-bis(diphenylphosphino)ferrocene]palladium (II) dichloride dichloromethane adduct (0.04 equivalents) were added, the mixture was stirred for 12 hours at 110° C. to implement Negishi coupling, and the following compound (4,13-diphenyl-diphenanthro[1,2-b:2',1'-d]thiophene) was obtained (yield of 95%).

[Chem. 20]

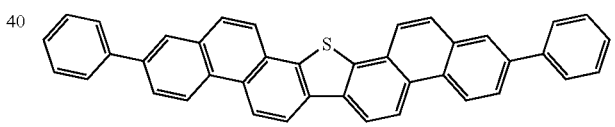

The results of the $T_{95}$ determined for this compound in the same manner as in Example 1 are shown in Table 1.

<Production and Evaluation of Polycrystalline Organic Thin-Film Transistor>

With the compound described above, a polycrystalline organic thin-film transistor was produced and evaluated in the same manner as in Example 1. As a substrate for measuring FET characteristics, a substrate having a thermal oxide film of $SiO_2$ (thickness: 500 nm) was prepared on a surface of a silicon substrate (thickness: 0.4 mm). The surface of the thermal oxide film of this substrate was treated with triethoxytridecafluorooctyl silane.

Next, the substrate for measuring FET characteristics was heated to 100° C., and the compound was vacuum deposited thereon to a thickness of 40 nm, and then 2 nm of 2,3,5,6-tetrafluoro-7,7,8,8-tetracyanoquinodimethane, which is an acceptor molecule, and 40 nm of gold were vapor deposited as an electrode using a shadow mask. A channel was molded by etching using a pulse laser with a wavelength of 355 nm to prevent the flow of current outside of the channel. The transmission characteristics were measured by sweeping the gate voltage in a range from +50 V to −150 V at a drain voltage of −150 V using the 4200-SCS semiconductor parameter analyzer available from Keithley Instruments, LLC. From the obtained transmission characteristics, the carrier mobility in the saturation region was determined from the IdVg measurement of the FET described above. In which of the below-described evaluation criteria ranges the calculated carrier mobility belongs was then determined. The evaluation results are shown in Table 2.

<Production and Evaluation of Monocrystalline Organic Thin-Film Transistor>

As a substrate for measuring FET characteristics, a substrate having a thermal oxide film of $SiO_2$ (thickness: 500 nm) was prepared on a surface of a silicon substrate (thickness: 0.4 mm). The surface of the thermal oxide film of this substrate was treated with triethoxytridecafluorooctyl silane.

With the compound described above, a monocrystalline organic thin-film transistor was produced and evaluated. A monocrystalline film of the abovementioned compound was obtained through the PVT method, and then affixed onto the abovementioned substrate for measuring FET characteristics, and then 2 nm of 2,3,5,6-tetrafluoro-7,7,8,8-tetracyanoquinodimethane, which is an acceptor molecule, and 40 nm of gold were vapor deposited as an electrode using a shadow mask designed for a channel length of 100 μm. A channel was molded by etching using a pulse laser with a wavelength of 355 nm to prevent the flow of current outside of the channel. The transmission characteristics were measured by sweeping the gate voltage in a range from +50 V to −150 V at a drain voltage of −150 V using the 4200-SCS semiconductor parameter analyzer available from Keithley Instruments, LLC. From the obtained transmission characteristics, the carrier mobility in the saturation region was determined from the IdVg measurement of the FET described above. In which of the below-described evaluation criteria ranges the calculated carrier mobility belongs was then determined. The evaluation results are shown in Table 2.

Example 3: 4,13-di-n-decyl-diphenanthro[1,2-b:2′,1′-d]thiophene

Steps 1 to 4 were implemented in the same manner as in Example 1, after which decylmagnesium bromide (4.0 equivalents) was added to the toluene solvent, the mixture was cooled to 0° C., and then zinc chloride (4.4 equivalents) and lithium chloride (4.4 equivalents) were added, and the mixture was stirred at 0° C. for 10 minutes. Next, the compound (1.0 equivalents) obtained in step 4 and a [1,1′-bis(diphenylphosphino)ferrocene]palladium (II) dichloride dichloromethane adduct (0.08 equivalents) were added, the mixture was stirred for 24 hours at 110° C. to implement Negishi coupling, and the following compound (4,13-di-n-decyl-diphenanthro[1,2-b:2′,1′-d]thiophene) was obtained (yield of 87%).

[Chem. 21]

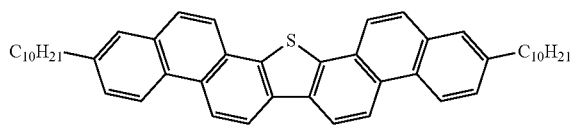

Figure 7:
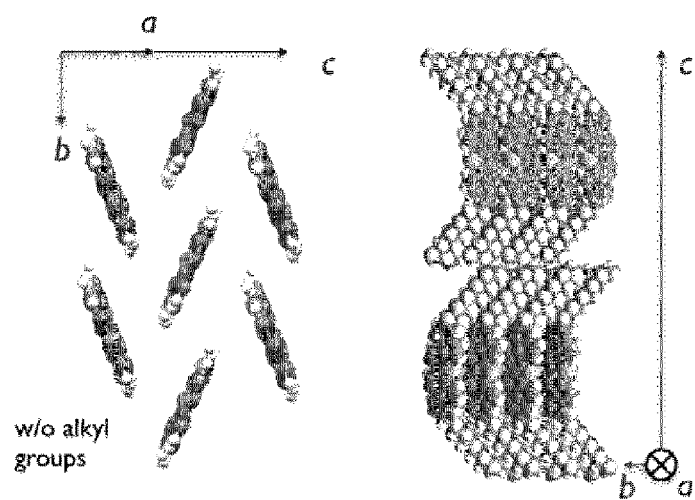
FIG. 7 illustrates the crystal structure and provides crystal data of a compound of Example 3.

Monocrystals of the above compound were obtained from a heated o-dichlorobenzene solution by gradually cooling, and then a monocrystal X-ray structural analysis was performed in the same manner as in Example 1. FIG. 7 illustrates the crystal structure of the compound and provides the crystal data thereof. As a result, it was confirmed that the monocrystal of the compound had a herringbone structure-type packing pattern. In addition, the results of the $T_{95}$ determined for this compound in the same manner as in Example 1 are also shown in Table 1.

<Production and Evaluation of Coated-Type Organic Monocrystal Thin-Film Transistor>

As a substrate for measuring FET characteristics, a substrate having a thermal oxide film of $SiO_2$ (thickness: 500 nm) was prepared on a surface of a silicon substrate (thickness: 0.4 mm). The surface of the thermal oxide film of this substrate was treated with triethoxytridecafluorooctyl silane.

Powder of the above compound was inserted into a beaker containing o-dichlorobenzene as a solvent, the concentration of the compound therein was adjusted to 0.05 wt. %, and the powder was completely dissolved by heating to 110° C. on a hot plate. The substrate for measuring FET characteristics was placed on a hot plate, and the obtained organic solution was coated onto the substrate thereof through edge-casting and heated to 70° C. to evaporate the solvent, and a monocrystalline organic semiconductor film was formed.

Next, numerous field-effect transistors were produced using the crystals that were formed into a film as an active layer, and the mobility was estimated from the transmission characteristics thereof. First, 2 nm of 2,3,5,6-tetrafluoro-7,7,8,8-tetracyanoquinodimethane, which is an acceptor molecule, and 50 nm of gold were vapor deposited as an electrode on the thin film using a shadow mask designed for a channel length of 200 μm. Next, doping was implemented by immersing the device in an acetonitrile solvent with 0.1 wt. % 2,3,5,6-tetrafluoro-7,7,8,8-tetracyanoquinodimethane, and the solvent was evaporated by heating to 50° C. on a hot plate. A channel was molded by etching using a pulse laser with a wavelength of 355 nm to prevent the flow of current outside of the channel. The transmission characteristics were measured by sweeping the gate voltage in a range from +50 V to −150 V at a drain voltage of −150 V using the 4200-SCS semiconductor parameter analyzer available from Keithley Instruments, LLC. From the obtained transmission characteristics, the carrier mobility in the saturation region was determined from the IdVg measurement of the FET described above. Note that the measurement of mobility varies depending on the direction of the current flowing in the active layer, but here, the direction of the channel was set for current to flow in the direction in which the mobility becomes the highest. In which of the following evaluation criteria ranges the calculated carrier mobility belongs was then determined. The evaluation results are shown in Table 2.

Example 4: 4,13-diphenylethyl-diphenanthro[1,2-b:2′,1′-d]thiophene

Steps 1 to 4 were implemented in the same manner as in Example 1, after which phenyethylmagnesium chloride (3.0 equivalents) was added to the toluene solvent, the mixture was cooled to 0° C., and then zinc chloride (3.2 equivalents) and lithium chloride (3.2 equivalents) were added, and the mixture was stirred at 0° C. for 10 minutes. Next, the compound (1.0 equivalents) obtained in step 4 and a [1,1′-bis(diphenylphosphino)ferrocene]palladium (II) dichloride dichloromethane adduct (0.05 equivalents) were added, the mixture was stirred for 9 hours at 110° C. to implement Negishi coupling, and the following compound (4,13-diphenyl-diphenanthro[1,2-b:2',1'-d]thiophene) was obtained (yield of 84%).

[Chem. 22]

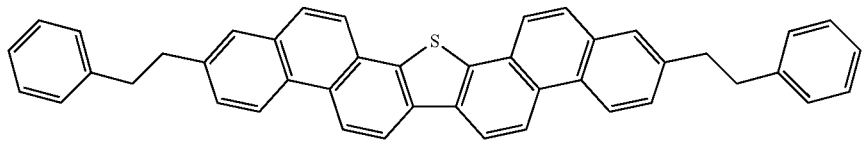

Figure 8:
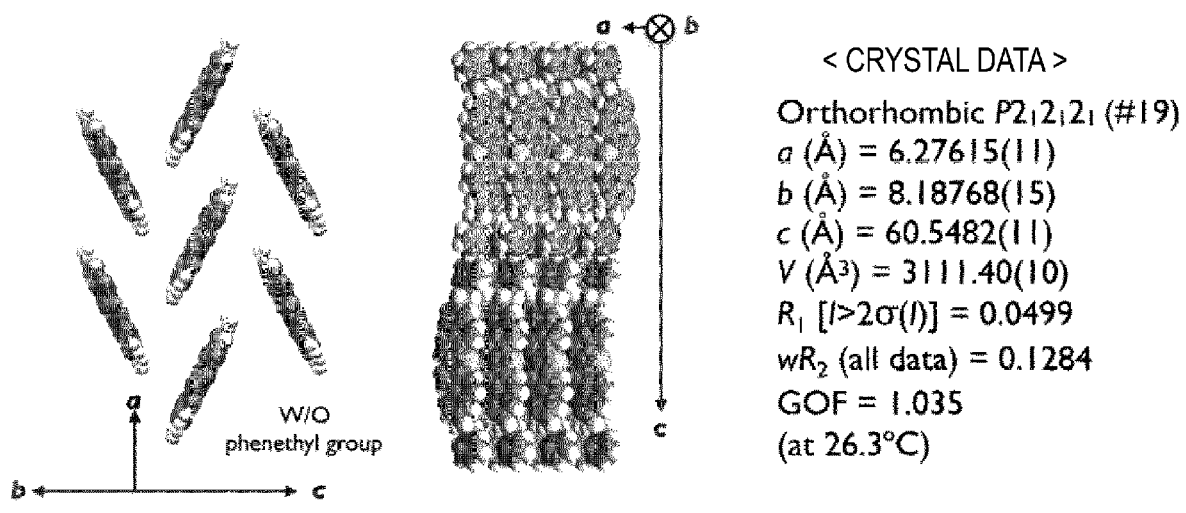
FIG. 8 illustrates the crystal structure and provides crystal data of a compound of Example 4.

Monocrystals of the above compound were obtained from a heated 1-chloronaphthalene solution by gradually cooling, and then a monocrystal X-ray structural analysis was performed in the same manner as in Example 1. FIG. 8 illustrates the crystal structure of the compound and provides the crystal data thereof. As a result, it was confirmed that the monocrystal of the compound had a herringbone structure-type packing pattern. In addition, the results of the $T_{95}$ determined for this compound in the same manner as in Example 1 are also shown in Table 1.

<Production and Evaluation of Coated-Type Organic Monocrystal Thin-Film Transistor>

As a substrate for measuring FET characteristics, a substrate having a thermal oxide film of $SiO_2$ (thickness: 500 nm) was prepared on a surface of a silicon substrate (thickness: 0.4 mm). The surface of the thermal oxide film of this substrate was treated with triethoxytridecafluorooctyl silane.

Powder of the above compound was inserted into a beaker containing 1-chloronaphthalene as a solvent, the concentration of the compound therein was adjusted to 0.01 wt. %, and the powder was completely dissolved by heating to 150° C. on a hot plate. The substrate for measuring FET characteristics was placed on a hot plate, and the obtained organic solution was coated onto the substrate thereof through edge-casting and heated to 120° C. to evaporate the solvent, and a monocrystalline organic semiconductor film was formed.

Next, numerous field-effect transistors were produced using the crystals that were formed into a film as an active layer, and the mobility was estimated from the transmission characteristics thereof. First, 2 nm of 2,3,5,6-tetrafluoro-7,7,8,8-tetracyanoquinodimethane, which is an acceptor molecule, and 50 nm of gold were vapor deposited as an electrode on the thin film using a shadow mask designed for a channel length of 200 μm. Next, doping was implemented by immersing the device in an acetonitrile solvent with 0.1 wt. % 2,3,5,6-tetrafluoro-7,7,8,8-tetracyanoquinodimethane, and the solvent was evaporated by heating to 50° C. on a hot plate. A channel was molded by etching using a pulse laser with a wavelength of 355 nm to prevent the flow of current outside of the channel. The transmission characteristics were measured by sweeping the gate voltage in a range from +50 V to −150 V at a drain voltage of −150 V using the 4200-SCS semiconductor parameter analyzer available from Keithley Instruments, LLC. From the obtained transmission characteristics, the carrier mobility in the saturation region was determined from the IdVg measurement of the FET described above. Note that the measurement of mobility varies depending on the direction of the current flowing in the active layer, but here, the direction of the channel was set for current to flow in the direction in which the mobility becomes the highest. In which of the below-described evaluation criteria ranges the calculated carrier mobility belongs was then determined. The evaluation results are shown in Table 2.

Comparative Example 1: Dinaphtho[1,2-b:2',1'-d]thiophene

The following compound (dinaphtho[1,2-b:2',1'-d]thiophene) described in Example 1 of patent document 2 (JP 2013-197193 A) was prepared.

[Chem. 23]

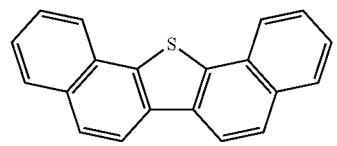

Figure 9:
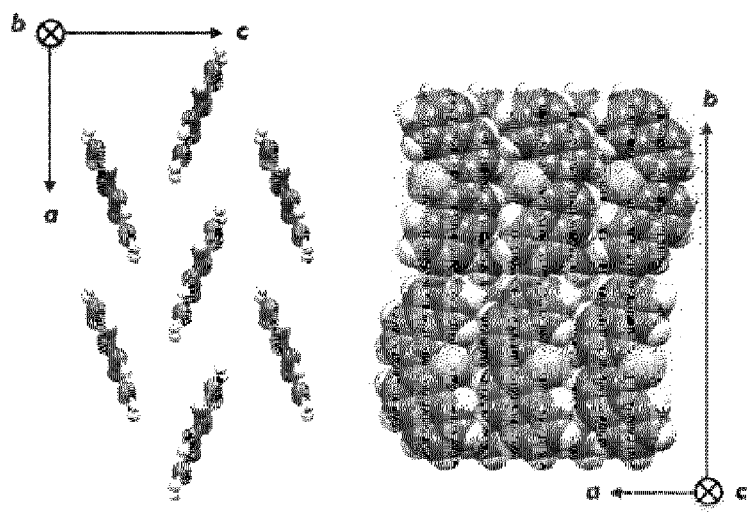
FIG. 9 illustrates the crystal structure and provides crystal data of a compound of Comparative Example 1.

Monocrystals of the above compound were obtained through a physical gas phase transport method, after which a monocrystal X-ray structural analysis was performed in the same manner as in Example 1. FIG. 9 illustrates the crystal structure of the compound and provides the crystal data thereof. As a result, it was confirmed that the monocrystal of the compound had a herringbone structure-type packing pattern. In addition, the results of the $T_{95}$ determined for this compound in the same manner as in Example 1 are also shown in Table 1.

<Production and Evaluation of Polycrystalline Organic Thin-Film Transistor>

With the compound described above, a polycrystalline organic thin-film transistor was produced and evaluated in the same manner as in Example 1. As a substrate for measuring FET characteristics, a substrate having a thermal oxide film of $SiO_2$ (thickness: 500 nm) was prepared on a surface of a silicon substrate (thickness: 0.4 mm). The surface of the thermal oxide film of this substrate was treated with decyltrimethoxysilane.

Next, the substrate for measuring FET characteristics was heated to 60° C., and the compound was vacuum deposited thereon to a thickness of 40 nm, and then 1 nm of 2,3,5,6-tetrafluoro-7,7,8,8-tetracyanoquinodimethane, which is an acceptor molecule, and 30 nm of gold were vapor deposited as an electrode using a shadow mask. A channel was molded by etching using a pulse laser with a wavelength of 355 nm to prevent the flow of current outside of the channel. The transmission characteristics were measured by sweeping the gate voltage in a range from +100 V to −100 V at a drain voltage of −100 V using the 4200-SCS semiconductor parameter analyzer available from Keithley Instruments, LLC. From the obtained transmission characteristics, the carrier mobility in the saturation region was determined from the IdVg measurement of the FET described above. In which of the below-described evaluation criteria ranges the calculated carrier mobility belongs was then determined. The evaluation results are shown in Table 2.

<Production and Evaluation of Monocrystalline Organic Thin-Film Transistor>

With the compound described above, a monocrystalline organic thin-film transistor was produced and evaluated in the same manner as in Example 2. A monocrystalline film of the abovementioned compound was obtained through the PVT method, and then affixed onto the same substrate for measuring FET characteristics as in Example 2, and then 1 nm of 2,3,5,6-tetrafluoro-7,7,8,8-tetracyanoquinodimethane, which is an acceptor molecule, and 30 nm of gold were vapor deposited as an electrode using a shadow mask designed for a channel length of 200 μm. A channel was molded by etching using a pulse laser with a wavelength of 355 nm to prevent the flow of current outside of the channel. The transmission characteristics were measured by sweeping the gate voltage in a range from +50 V to −150 V at a drain voltage of −150 V using the 4200-SCS semiconductor parameter analyzer available from Keithley Instruments, LLC. From the obtained transmission characteristics, the carrier mobility in the saturation region was determined from the IdVg measurement of the FET described above. In which of the below-described evaluation criteria ranges the calculated carrier mobility belongs was then determined. The evaluation results are shown in Table 2.

TABLE 1

|  | T95: 5% Weight loss temperature (° C.) |
| --- | --- |
| Example 1 | 375 |
| Example 2 | 494 |
| Example 3 | 419 |
| Example 4 | 459 |
| Comparative Example 1 | 266 |

Evaluation Criteria
A: $5.1 \times 10^0$ cm$^2$/Vs or greater
B: From $3.1 \times 10^0$ cm 2/Vs to less than $5.1 \times 10^0$ cm$^2$/Vs
C: From $1.1 \times 10^{-1}$ cm$^2$/Vs to less than $3.1 \times 10^0$ cm$^2$/Vs
D: From $1.1 \times 10^{-2}$ cm$^2$/Vs to less than $1.1 \times 10^{-1}$ cm$^2$/Vs
E: Less than $1.1 \times 10^{-2}$ cm$^2$/Vs

TABLE 2

|  | Carrier Mobility | |
| --- | --- | --- |
|  | Monocrystal | Polycrystal (Vapor deposition) |
| Example 1 | — | D |
| Example 2 | B | D |
| Example 3 | A | — |
| Example 4 | A | — |
| Comparative Example 1 | C | E |

From the results in Table 2, the following is understood.
The organic thin-film transistor that used the monocrystal in Comparative Example 1 exhibited high carrier mobility and functioned as an organic thin-film transistor. On the other hand, the organic thin-film transistor formed through vapor deposition in Comparative Example 1 exhibited low carrier mobility and could not be preferably used to function as an organic thin-film transistor.

In contrast, the polycrystalline organic thin-film transistors formed through vapor deposition in Examples 1 and 2 according to embodiments of the present invention exhibited high mobility and functioned as organic thin-film transistors. Furthermore, it was found that compared to the organic thin-film transistor that used the monocrystal of Comparative Example 1, the organic thin-film transistor that used the monocrystal of Example 2 exhibited a higher carrier mobility, and could be preferably used as an organic semiconductor material. It was also found that the monocrystalline organic thin-film transistors obtained through coating in Examples 3 and 4 also exhibited a high carrier mobility and could be preferably used as organic semiconductor materials.

Example 5: 3,7-dibromo-4,6-diformyldibenzothiophene 4,6-Diformyldibenzothiophene was obtained through the same procedures as in step 1 described in Example 1, after which the following steps 2 and 3 were performed in that order.

Step 2: A mixed solvent of 1,2-dichloroethane and trifluoroacetic acid at a volume ratio of 1:1 was added to a mixture of 4,6-diformyldibenzothiophene (1.0 equivalent), N-bromosuccinimide (6.2 equivalents), 4-nitroanthranilic acid (1.0 equivalent), palladium (II) acetate (0.1 equivuivalents), silver trifluoroacetate (AgTFA) (0.1 equivalents), and p-toluenesulfonic acid monohydrate (2.0 equivalents) with the concentration of the 4,6-diformyldibenzothiophene being 0.1 M, the mixture was reacted for 12 hours at 90° C., and the following (3,7-dibromo-4,6-diformyldibenzothiophene) was obtained (yield of 83%).

[Chem. 24]

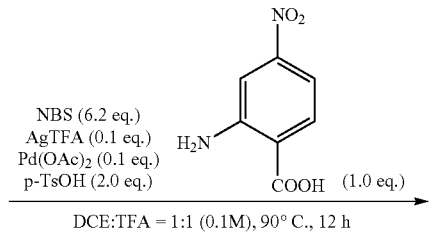

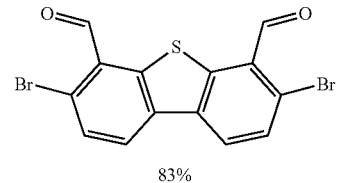

83%

Step 3: The 3,7-dibromo-4,6-diformyldibenzothiophene (1.0 equivalent), phenyltrimethylstannane (3.0 equivalents), and tetrakis(triphenylphosphine)palladium(O) (0.05 equivalents) were added, and the mixture was reacted for 48 hours at 110° C., and the following (3,7-diphenyl-4,6-diformyldibenzothiophene) (yield of 79%) was obtained.

[Chem. 25]

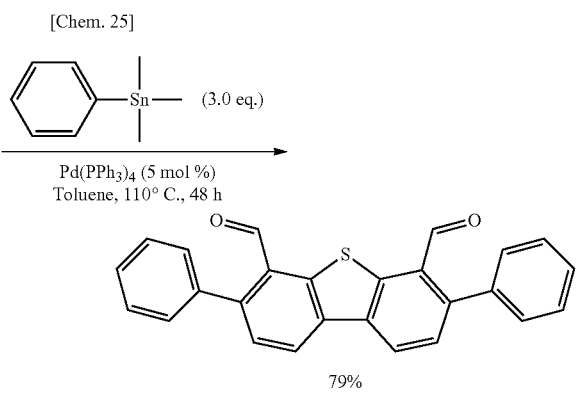

79%

Regarding the 3,7-diphenyl-4,6-diformyldibenzothiophene described above, by cyclizing the vinyl ether moiety using the same method described in steps 3 and 4 of Example 1, the [1,2-b:2',1'-d]thiophene of Example 1 can be synthesized.

REFERENCE SIGNS LIST

1 Substrate
2 Contact member
2a End surface
3 Droplet
4 Semiconductor film
5 Raw material solution
6 Solution supply nozzle
12 Gate electrode
13 Insulating film
14A Source electrode
14B Drain electrode
15 Organic semiconductor film
16 Carrier injection layer
17 Self-assembled monomolecular film

The invention claimed is:

1. A compound represented by Formula (1a) or Formula (1b) below:

[Chem. 1]

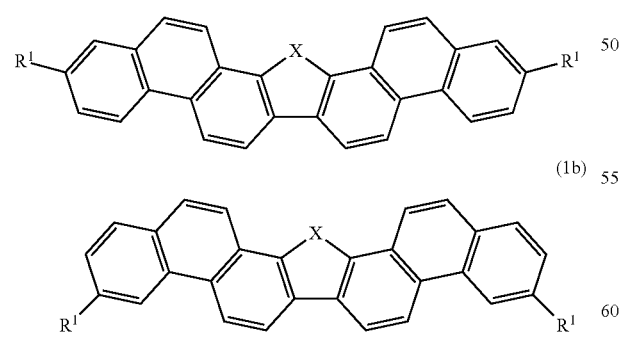

where in Formulas (1a) and (1b), X represents S, and $R^1$ each independently represents a hydrogen atom, a halogen atom, an alkyl group, an aryl group, an aralkyl group, a pyridyl group, a furyl group, a thienyl group, or a thiazolyl group.

2. The compound according to claim 1, wherein $R^1$ each independently represents a phenylalkyl group or an alkylphenyl group.

3. The compound according to claim 1, wherein $R^1$ each independently represents a phenylalkyl group having from 7 to 16 carbons, or an alkylphenyl group having from 7 to 16 carbons.

4. The compound according to claim 1, wherein $R^1$ each independently represents a phenylalkyl group having from 7 to 16 carbons.

5. The compound according to claim 1, wherein $R^1$ each independently represents an alkyl group having from 1 to 14 carbons.

6. The compound according to claim 1, wherein $R^1$ each independently represents a halogen atom.

7. The compound according to claim 1, wherein a temperature at which a weight loss percentage with heating becomes 5% in thermogravimetric measurements when the temperature is increased from normal temperature at a temperature increasing rate of 5° C./minute in a nitrogen atmosphere is 350° C. or higher.

8. An organic semiconductor material comprising the compound described in claim 1.

9. An organic semiconductor film comprising the compound described in claim 1.

10. An organic field-effect transistor comprising a substrate, a gate electrode, a gate insulating film, a source electrode, a drain electrode, and an organic semiconductor layer, wherein the organic semiconductor layer includes an organic semiconductor film described in claim 9.

11. A compound represented by Formula (X) below:

[Chem. 2]

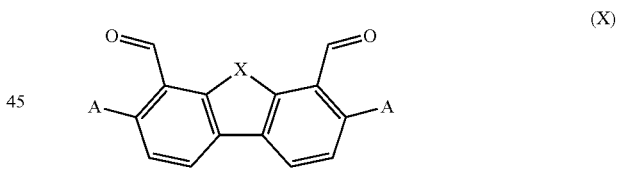

where in Formula (X), X represents S, and A each independently represents a halogen atom.

12. A compound represented by Formula (2a) or Formula (2b) below:

[Chem. 3]

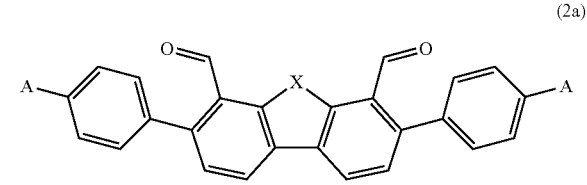

-continued
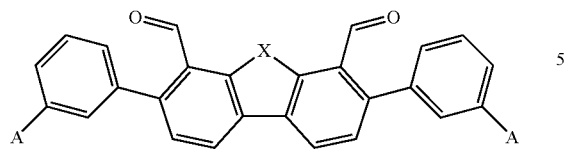
(2b)
where in Formulas (2a) and (2b), X represents S, O or Se, and A each independently represents a halogen atom or a hydrogen atom.
* * * * *